United States Patent [19]
Vonier et al.

[11] Patent Number: 5,564,552
[45] Date of Patent: Oct. 15, 1996

[54] APPARATUS FOR LOADING CONDOMS ONTO MANDRELS

[75] Inventors: Nathan Vonier, Hermitage, Tenn.; Jim Whitten, Albany, Ga.

[73] Assignee: Agri Dynamics, Inc., Albany, Ga.

[21] Appl. No.: 334,415

[22] Filed: Nov. 4, 1994

[51] Int. Cl.⁶ ............................................. B65G 35/00
[52] U.S. Cl. ........................... 198/409; 198/803.12
[58] Field of Search ............................. 198/409, 468.6, 198/487.1, 803.12

[56] References Cited

U.S. PATENT DOCUMENTS

| | | | |
|---|---|---|---|
| 2,953,239 | 9/1960 | Garman et al. | 198/468.6 X |
| 3,033,342 | 5/1962 | Kinnicutt, Jr. | 198/803.12 X |
| 3,083,813 | 4/1963 | Lusher | 198/803.12 X |
| 3,868,899 | 3/1975 | Nye et al. | 198/803.12 X |
| 4,262,795 | 4/1981 | Hecker | 198/803.12 X |
| 4,740,134 | 4/1988 | Dixon | 198/468.6 X |
| 4,822,448 | 4/1989 | Thompson et al. | 198/487.1 X |
| 5,147,026 | 9/1992 | Scaglra | 198/468.6 X |
| 5,348,134 | 9/1994 | Wadell | 198/468.6 X |

*Primary Examiner*—David A. Bucci
*Attorney, Agent, or Firm*—Thomas C. Saitta

[57] ABSTRACT

An apparatus for loading condoms onto mandrels is disclosed, the apparatus comprising a number of expansion rods adapted to receive and stretch a condom, the rods being mounted on a reciprocating carriage assembly which moves the rods past the mandrel, the mandrel itself stripping the condom from the rods.

13 Claims, 2 Drawing Sheets

APPARATUS FOR LOADING CONDOMS ONTO MANDRELS

BACKGROUND OF THE INVENTION

The invention relates generally to the field of apparatus for loading condoms onto mandrels. More particularly, the invention relates to a condom loading apparatus utilizing a number of rods to expand the condom as it is drawn down onto the mandrel.

The handling of condoms by mechanized means has long been a problem within the industry. Because condoms are elastic, non-rigid devices made of thin-walled latex or similar materials with no particular configuration unless supported or held by outside means, few if any devices have been developed which can successfully perform handling operations, such that most handling operations are be necessity carried out by hand. For example, each condom must be tested for the presence of minute holes after manufacture. This is done by stretching each condom by hand onto a metal mandrel of appropriate shape. The condom is then passed over an electrically charged net. If any current passes from the net to the mandrel, the condom is rejected.

It is an object of this invention to provide an apparatus which can mechanically load a condom onto a mandrel. It is a further object of this invention to provide such an apparatus which utilizes expansion rods mounted on a movable carriage to stretch the condom onto the mandrel, whereby the condom is positioned on the expansion rods and the carriage is moved in a linear motion to load the mandrel and then clear into a retracted position, such that the loaded mandrel can then be moved for testing.

SUMMARY OF THE INVENTION

The invention comprises in general an apparatus having mandrel loading means mounted onto a track, the loading means comprising a number of expansion rods which occupy a relatively restricted area in the rest position in order to receive a condom, but which can be expanded around the mandrel to stretch the condom onto the mandrel. The configuration of the carriage and mount holding the expansion rods allows the carriage to be passed over the length of the mandrel into a recessed position to allow subsequent movement of the loaded mandrel for testing purposes. The carriage is mounted onto a track such that it receives the condom from a condom retaining means at the uppermost portion of the track and is brought downward on a line such that the central axis of the group of expansion rods is on the same line as the central axis of a mandrel in the loading position. The mandrel expands the expansion rods, thereby stretching the condom. The movement of the carriage down and past the mandrel strips the condom onto the mandrel, and the mandrel can now be moved for testing and the carriage returned to the upper position. This cycle is then repeated for successive condoms.

DETAILED DESCRIPTION OF THE INVENTION

Figure 1:
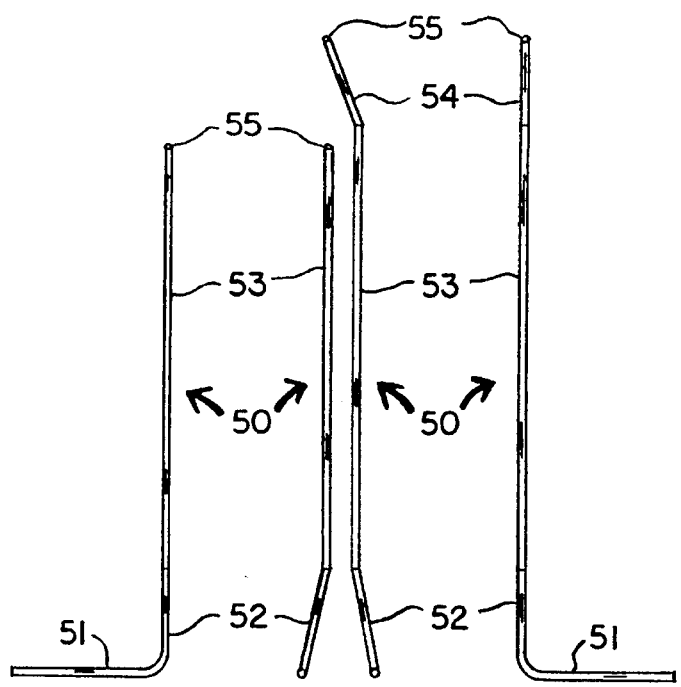
FIG. 1 is a combination of front and side views of the two types of expansion rod configurations.

With reference now to the drawings, the invention will be described in detail with regard to the best mode and preferred embodiment. The invention is an apparatus for loading condoms 90 onto a mandrel 91 which is shaped in matching configuration to the condom 90 and comprises a movable carriage assembly 60 upon which are mounted a number of expansion rods 50 for receiving and stretching a condom 90, whereby the condom 90 is deposited onto the mandrel 91 by movement of the carriage 60. The expansion rods 50 act as runners on the surface of the mandrel 91, such that there is no resistance or contact between the mandrel 91 and the condom 60 until the tip of the condom 90 is brought down onto the tip of the mandrel 91.

Figure 3:
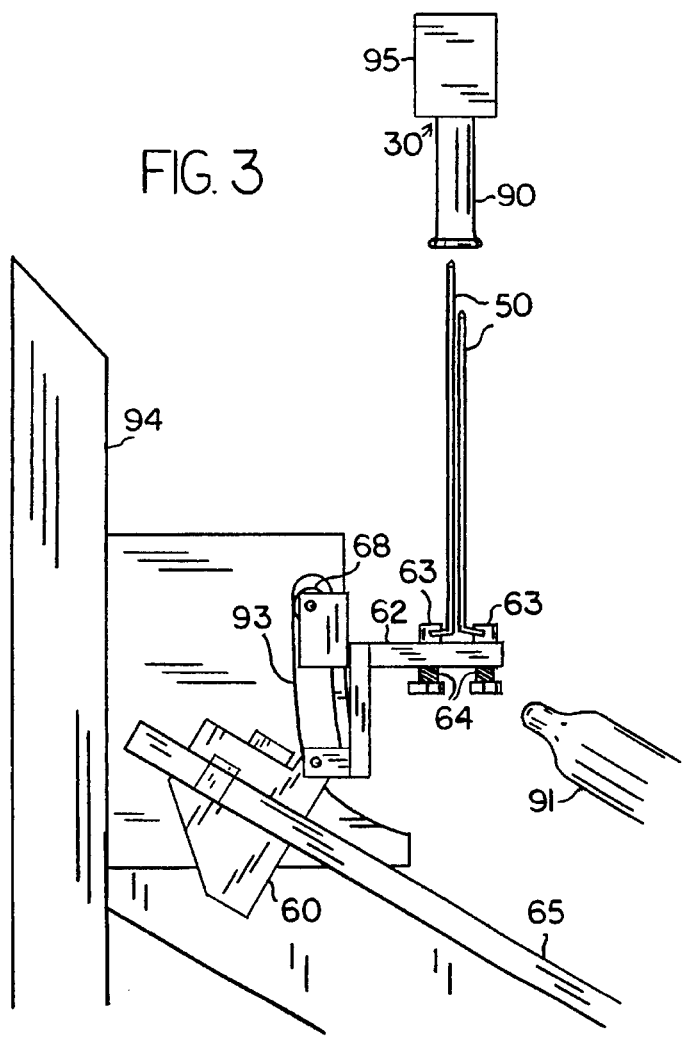
FIG. 3 is a view of the rod carriage in the receiving position.

The carriage assembly 60 and expansion rods 50 can be seen in FIG. 3. This illustration shows the rods 50 in the receiving position to receive the condom 90 prior to loading it onto the mandrel 91. The carriage assembly 60 is comprised of a rod mount 62 to which are attached the multiple expansion rods 50. The carriage assembly 60 is mounted onto a linear carriage track 65 which allows reciprocal movement of the carriage 60 past the mandrel 91 to be loaded. Condom retaining means 30 holds the condom 90 is a vertical position with the tip of the condom 90 on top so that the base, ring and open end of the condom 90 hang downward. Condom retaining means 30 can be any suitable mechanism for presenting the condom 90 in the described manner, and can comprise mechanical or suction means 95 to hold the tip for release and to keep the body expanded to allow for insertion of the expansion rods 50 into the condom 90. Alternatively and preferably, it has been found that simply maintaining the tip of the condom 90 at the uppermost position and then releasing it to fall onto the expansion rods 50 is the simplest and most efficient way to place the condom 90 onto the expansion rods 50. As the condom 90 falls, air fills the interior through the open end, thus expanding the condom 90 like a parachute to settle onto the rods 50.

Figure 2:
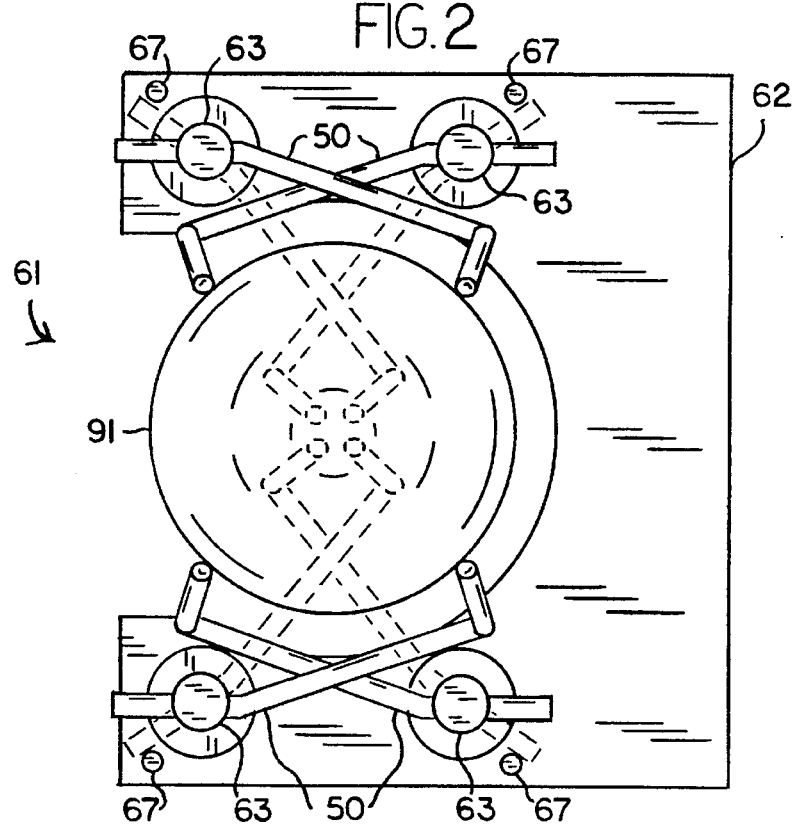
FIG. 2 is a view illustrating the initial receiving positioning of the expansion rods and the mandrel loading positioning.

Expansion rods 50 are preferably thin, elongated members of small cross-sectional diameter composed of a rigid metal or like material. While rods 50 may be configured in many various shapes, the configuration shown in FIGS. 1 and 2 has been found to be very effective in loading the condom 90 onto the mandrel 91. It is best to use at least three, and preferably four or more rods 50 to expand the condom 90 as it is drawn over the mandrel 91. The object is to minimize and preferably completely eliminate any contact between the sides of the mandrel 91 and the sides of the condom 90. The use of four rods 50 positioned 90 degrees apart in the expanded configuration is preferred. The rods 50 are pivotally mounted onto a generally U-shaped mount 62 surrounding a mandrel receiving opening 61. The connecting segment 51 of each rod 50 is attached to a pivoting post 63, which is biased by a spring 64 such that the rods 50 occupy a rest position, shown by the dotted lines in FIG. 2, with the tips 55 of all the rods 50 being relatively contiguous or adjacent to one another and the main body segments 53 being generally parallel and also contiguous or adjacent each other. A positioning pin 67 is used to maintain the rods 50 in this position. It is necessary that the tips 55 occupy a relatively small area so that they will not interfere with the drop of the condom 90, as the tip of the condom 90 should end up resting on the tips 55 of the rods 50. In the preferred configuration, as seen in FIG. 1, each rod 50 is comprised of a connecting segment 51 for insertion into the pivoting posts 63, a main body segment 53, a transition segment 52 joining the main body 53 and the connecting segment 51 angled such that the central axis of the main body segment 53 does not intersect the central axis of the connecting segment 51, and a blunt or rounded tip 55. Preferably, one rod 50 is slightly longer than the others and is provided with a centering extension segment 54, whereby the tip 55 of this rod 50 is positioned on the central axis of the grouping of all the rods 50. This results in only a single uppermost tip 55, thus insuring that the condom 90 will not be snagged as it is dropped onto the rods 50. This configuration is preferred as it enables the main body segment 53 of each rod 50 to remain parallel to the sides of the mandrel 91 as they are passed down over it.

Figure 4:
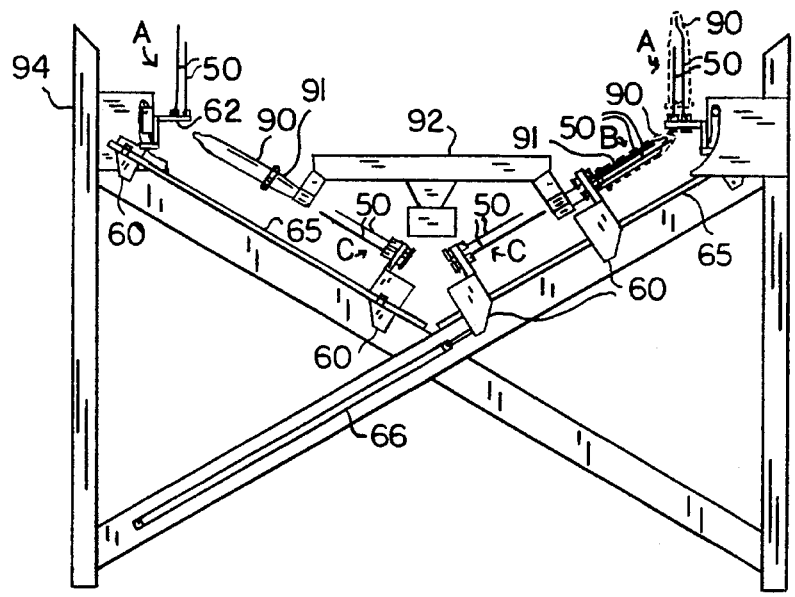
FIG. 4 is a view of the loading apparatus showing rod carriages in various positions of the loading cycle.

FIG. 4 shows an apparatus with two carriage tracks 65. A reciprocating means 66, such as an air cylinder, mounted onto a frame 94 moves each carriage 60 up and down track 65. Three positions A, B and C are illustrated. Position A is the receiving position previously described at which the condom 90 is placed onto the expansion rods 50. Position B is the mandrel loading position, and position C is the retracted position. After the condom 90 is placed onto the rods 50, the carriage is moved down along track 65 to mandrel 91. The mandrel receiving opening 61 is positioned opposite from the connecting means attaching the carriage 60 to the track 65, in the upward orientation as shown. The mandrel 91 is mounted so as to depend from a mandrel shuttle 92, with the connecting means being on top of the mandrel 91. As the carriage assembly 60 is brought down to mandrel 91, it freely passes the mandrel 91 because of the mandrel receiving opening 61. As the tip of the mandrel 91 encounters the transition segments 52 of the rods 50, they are forced outward to the positions shown by the solid lines in FIG. 2. This stretches the condom 90 to a size greater than the outer circumference of the mandrel 91, the main body segments 53 of the rods 50 acting as runners and spacers along the length of the mandrel 91. As the carriage 60 is brought lower, the tip of the mandrel 91 encounters the tip of the condom 90 and acts as an anchor, as shown in position B of FIG. 4. The carriage 60 continues downward and the expansion rods 50 are pulled out of the condom 90, leaving the condom 90 fully loaded onto the mandrel 91. With the carriage 60 now in the fully retracted position C, the mandrel shuttle 92 can move the loaded mandrel 91 to the testing and then the condom removal position. When mandrel 91 is moved away from track 65, the carriage 60 is returned to the receiving position A for another cycle.

As explained, it is preferable that the rods 50 be in a vertical position to receive the condom 90, especially when the gravity drop method is utilized. For removal of the condom 90 from the mandrel 91 after testing, however, it is preferred that the mandrel 91 be non-vertically oriented. As shown in FIG. 4, this requires that the expansion rods 50 be repositioned from the vertical alignment of position A to the alignment of position B which matches the mandrel 91 alignment. In this embodiment, this realignment is accomplished by pivotally attaching the rod mount 62 to carriage 60 and positioning a roller 68 which enters an orienting slot 93 on frame 94 at the upper end of track 65. As carriage assembly 60 is moved upward by reciprocating means 66, the roller 68 pivots the mount 62 such that the rods 50 are vertically aligned. As the carriage 60 is lowered, the mount 62 pivots back into its resting position and the rods 50 are aligned with mandrel 91.

It is understood that equivalents and substitutions to elements or components set forth above may be obvious to those skilled in the art. The full scope and definition of the invention therefore is to be as set forth in the following claims.

We claim:

1. An apparatus for loading a condom onto a mandrel, said apparatus comprising a carriage assembly comprising a number of expansion rods attached to a mount, said expansion rods each comprising a main body segment and tip, whereby said main body segments and said tips of said rods are positioned adjacent each other in a rest position to receive a condom, but are expanded outward by passing said carriage assembly over a mandrel such that said rods expand said condom to a size greater than said mandrel, said carriage assembly being adapted to pass completely over said mandrel such that said mandrel removes said condom from said rods and said condom is retained on said mandrel.

2. The apparatus of claim 1, where said rods are pivotally connected to said mount.

3. The apparatus of claim 1, where said carriage assembly is mounted onto a track, and further comprising means to move said carriage assembly along said track.

4. The apparatus of claim 3, where said track is positioned on an incline, and further comprising means to alter the alignment of said expansion rods from a vertical orientation to a non-vertical orientation.

5. The apparatus of claim 4, where said means to alter alignment comprises a roller connected to said mount and a roller orienting slot.

6. The apparatus of claim 1, where one said expansion rod is longer than the other said expansion rods.

7. An apparatus for loading a condom onto a mandrel, said apparatus comprising:

(A) a carriage assembly comprising a mount and a plural number of expansion rods connected to said mount, said mount comprising a mandrel receiving opening adapted to allow the mount to be passed over a mandrel;

(B) said expansion rods each comprising a main body segment and a tip, where said rods are connected to said mount such that said rods are expandable by said mandrel from a rest position where each said main body segment and each said tip are adjacent each other for receiving a condom to an expanded position surrounding said mandrel when said mount is passed over said mandrel for the loading of said condom onto said mandrel.

8. The apparatus of claim 7, where said main body segments of said rods are substantially parallel to one another.

9. The apparatus of claim 8, where one said rod is longer than the other said rods.

10. The apparatus of claim 7, where said rods are pivotally connected to said mount.

11. The apparatus of claim 7 where said rod further comprise a transition segment, such that said mandrel contacts said transition segment to expand said rods when said mount is passed over said mandrel.

12. The apparatus of claim 7, where said rods extend vertically in said rest position to receive said condom.

13. The apparatus of claim 12, where said carriage assembly is mounted onto a non-vertical track, and further comprising means to alter the alignment of said mount form vertical to non-vertical.

\* \* \* \* \*